United States Patent [19]

Matyas

[11] Patent Number: 5,336,204
[45] Date of Patent: Aug. 9, 1994

[54] PROTECTIVE COVER FOR AN INFUSION DEVICE

[76] Inventor: Melanie E. Matyas, 301 N. Duane Ave., San Gabriel, Calif. 91775

[21] Appl. No.: 61,025

[22] Filed: May 14, 1993

[51] Int. Cl.⁵ .................................................. A61M 5/00
[52] U.S. Cl. ............................... 604/263; 128/888; 128/DIG. 26
[58] Field of Search .............. 128/888, DIG. 26, 846; 604/263, 304–308, 289, 290, 192; 602/41–45, 52, 53, 54, 3

[56] References Cited

U.S. PATENT DOCUMENTS

| | | | |
|---|---|---|---|
| 2,244,871 | 6/1941 | Guinzburg . | |
| 3,657,741 | 4/1972 | Blance . | |
| 3,782,378 | 1/1974 | Page ..................................... | 128/888 |
| 3,900,026 | 8/1975 | Wagner ................................ | 128/888 |
| 4,346,699 | 8/1982 | Little . | |
| 4,679,553 | 7/1987 | Proulx et al. ........................ | 128/846 |
| 4,726,364 | 2/1988 | Wylan .................................. | 602/44 |
| 5,209,718 | 5/1993 | McDaniel ............................ | 602/53 |

*Primary Examiner*—C. Fred Rosenbaum
*Assistant Examiner*—V. Alexander
*Attorney, Agent, or Firm*—Harlan P. Heubner

[57] ABSTRACT

A replaceable plastic protective cover to prevent damages to and to waterproof an infusion device attached to a person for receipt of periodic doses of drugs wherein the cover includes an annular flange with waterproof adhesive therearound to affix the same to the skin and a housing extends upward from said flange with a closable opening for access to the interior of the housing.

9 Claims, 2 Drawing Sheets

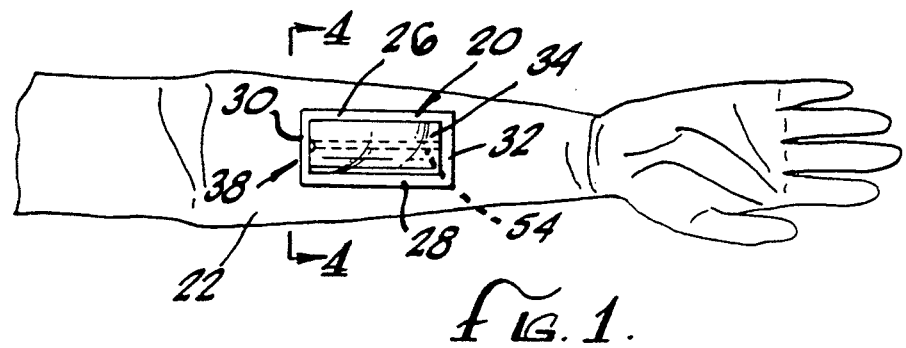
fig.1.
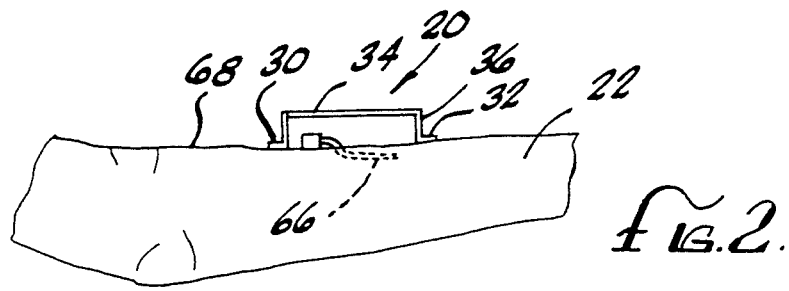
fig.2.
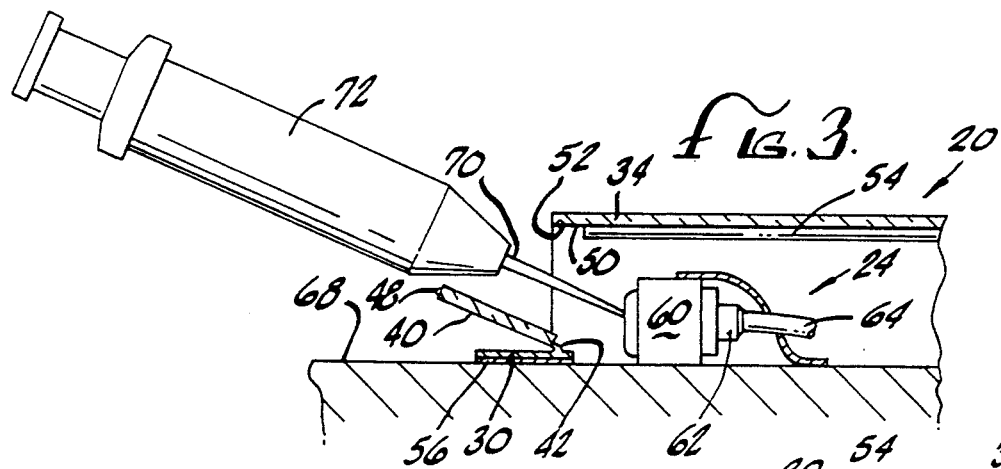
fig.3.
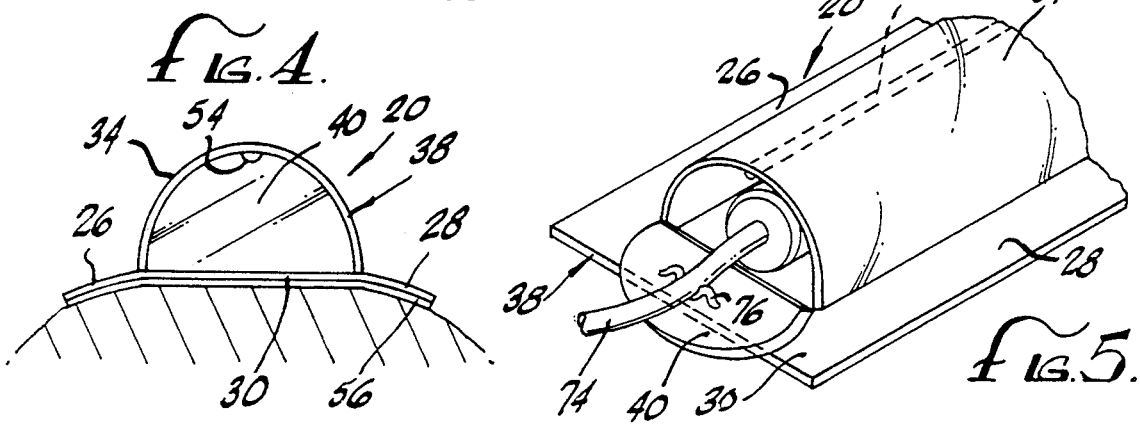
fig.4.
fig.5.

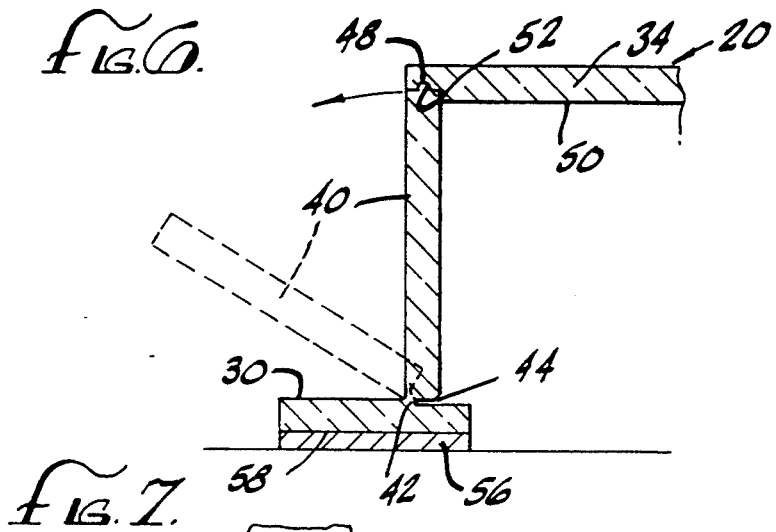
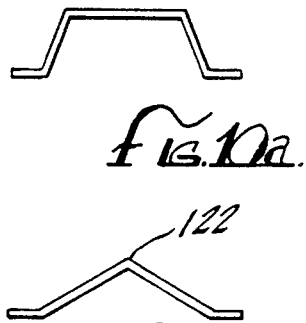
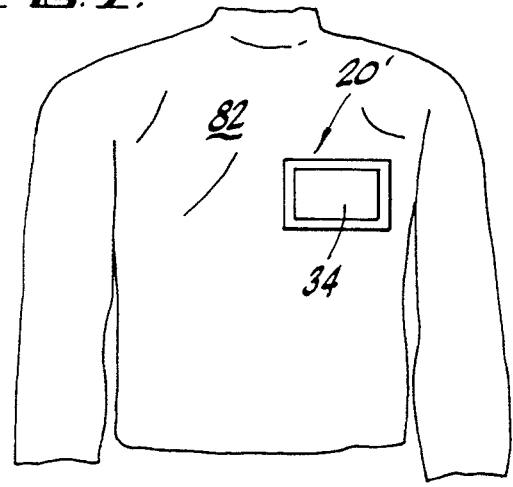
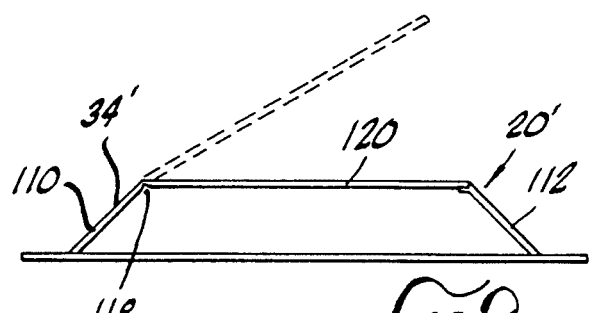
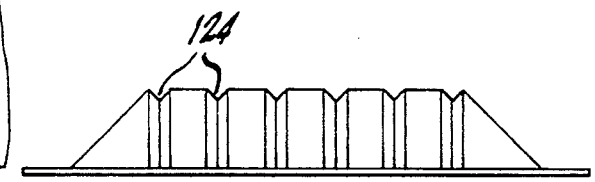
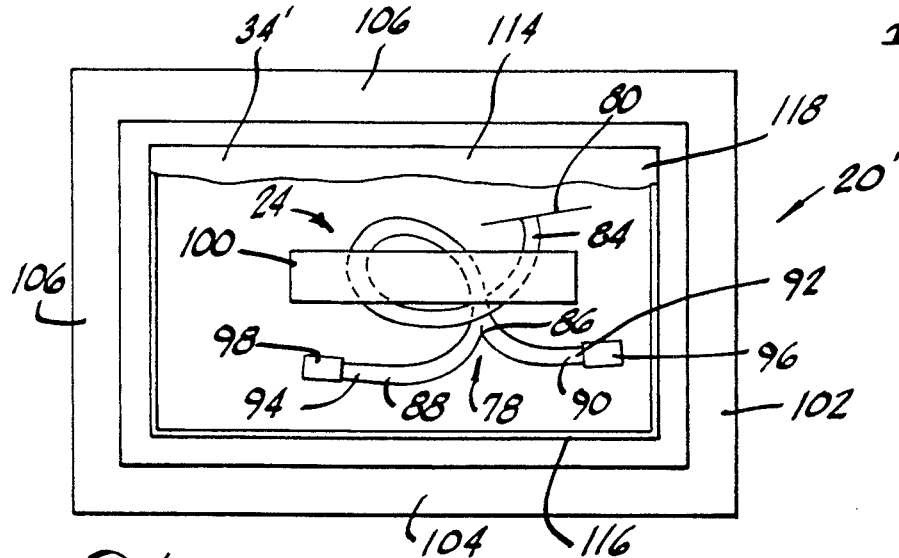

PROTECTIVE COVER FOR AN INFUSION DEVICE

BACKGROUND OF THE INVENTION

1. Field of the Invention

This invention relates to a protective cover for an infusion device that is positioned on a person over the device to protect a dislodgment and to waterproof the same.

2. Description of the Prior Art

With the use of an infusion device, such as a Heparin lock or subclavian catheter, that has a needle and tubing it is usually preferable to leave the same inserted within an arm or body of a person. This is particularly true with patients that have blood problems and must have Heparin administered in frequent doses. Also other illnesses may require frequent doses of a drug and thus the need to have a permanent or semi-permanent catheter or lock where the drug may be injected into the body. With the placement of the infusion device it is not necessary to make frequent skin insertions or incisions.

Heretofore there has not been any truly effective covers to protect infusion devices from dislodgment damages or water soaking. Bandages have been used to cover the devices but if it gets wet it has to be replaced. Also there is no structural strength offered by a bandage. The replacement is time consuming for a nurse or the patient and also curtails the ability to take full showers.

The glove of U.S. Pat. No. 4,346,699 again has the disadvantage of not protecting a wound or catheter from damage. Further, U.S. Pat. No. 3,657,741 suffers the same disadvantage as well as requiring a covering of a large area that might not have to be included. U.S. Pat. No. 2,244,871 also makes no provision for protecting a catheter from damage or dislodgment.

In addition some nurses have improvised protective covers from water by using plastic bags taped or tied to a patient. These at best are only temporary, time consuming to apply and again do not address the issue of damage, dislodgment, or truly keep the catheter free from water soaking.

SUMMARY OF THE INVENTION

One of the objects of the present invention is to provide a replaceable protective cover for infusion devices that is preferably made of clear plastic that may adhere to a patient wherein the device is waterproof.

Another object of the present invention is to provide a protective cover for infusion devices that is plastic and raised above the catheter to offer structural support to protect the infusion device from damage if the patient should roll over on the device.

A still further object of the present invention is to provide a protective cover that includes releasable adhesive wherein the device may be fixed to the skin of a patient to prevent dislodgment of the device and to forth a waterproof seal around the devices, yet be yieldable to be removed and replaced.

A yet further object of the present invention is to provide a protective cover that includes access means so that the infusion device becomes accessible for administering a drug into the device and in turn into the patient's body.

Another object of the present invention is to provide a protective cover for an infusion device that is relatively inexpensive and easy to install.

These and other objects and advantages will become apparent from the following part of the specification wherein details have been described for the competence of disclosure, without intending to limit the scope of the invention which is setforth in the appended claims.

BRIEF DESCRIPTION OF THE DRAWINGS

These advantages may be more clearly understood from the following detailed description and by reference to the drawings in which:

FIG. 1 is a top plan view of one form of the present invention as it might appear on the forearm of a patient;

FIG. 2 is a side view of the present invention as it might appear on the forearm of a patient;

FIG. 3 is an enlarged sectional view of one form of infusion device and a syringe;

FIG. 4 is an end view taken on line 4—4 of FIG. 1;

FIG. 5 is a prospective view of the invention as illustrated in FIGS. 1-4;

FIG. 6 is an enlarged sectional view of a hinged waterproof door that may be provided for access into the protective cover;

FIG. 7 is a modified form of protective cover for use with a subclavian catheter for the heart;

FIG. 8 is an enlarged view of the device and cover as illustrated in FIG. 7;

FIG. 9 is a protective device with a different location for a hinge access door;

FIGS. 10a and 10b are cross sectional views of protection devices of different configurations; and FIG. 11 another form of protection device with stiffening ribs therealong.

DETAILED DESCRIPTION OF THE PREFERRED EMBODIMENT

In FIG. 1 there is illustrated an infusion protective cover generally designated 20 mounted on the forearm 22 of a person to protect an infusion device designated 24.

The cover 20 is preferably made of clear plastic to view the interior for visibility of the catheter entry site and for signs and symptoms of infiltration or dislodgment and includes a pair of opposed flanges 26 and 28 and a second pair of opposed flanges 30 and 32 normal to the flanges 26 and 28. The flanges all form on annular flange around the cover 20.

In the embodiment of FIGS. 1-5 there is an arcuate of domed housing 34 that extends upward from the flanges 26-32. In addition, there is a sealed end 36 and a rearward hinged end designated 38.

The hinged end includes a door portion 40 that is hinged at 42 as by a living hinge of plastic where the door 40 and flange 30 are one piece with a cut 44 in the thickness of the door to form the hinge. See FIG. 6 for an exploded view of the door structure and the thinning of the plastic.

In order to maintain the door 40 in a closed position and to help waterproof the structure a locking means of an arcuate locking bead or tongue 46 may be provided on the arcuate edge 48 of the door 40. The dome housing 34 is provided on its interior surface 50 with a groove 52 to receive the bead 46.

The plastic of the dome or arcuate housing 34 may be stiff enough to not collapse without undue pressure but to further insure stability and strengthening a stabilizing rod 54 could be molded into the housing at the crown and depending downward from the interior surface 50. In the preferred embodiment the plastic material is resilient and flexible enough to be pinched to grip the device 24 to stabilize the same whereby a syringe 72 may be inserted in the device 24. Also by pinching the plastic between the fingers, the door 40 may be opened by the pressure. When the pressure is released the dome will return to its original shape.

The flanges 28-32 are all provided with a releasable, waterproof adhesive 56 to the under surface 58. The adhesive 56 should be of the type to adhere to human skin without taking part of the skin away when the device is removed.

In FIGS. 2, 3 and 5 there is illustrated a conventional type of intravenous assembly or infusion device 24 such as Heparin Lock 60 occupying a relatively small horizontal area that would include a coupling 62 for tube 64 that runs to a catheter needle 66 inserted below the skin 68 of arm 22 or other part of the body. The lock 60 is adapted to receive the needle end 70 of a conventional syringe 72.

Thus in the case of Heparin users with the device 24 secured to the forearm 22 by the adhesive 56, the door 40 is opened and the syringe 72 maybe inserted into the lock 60 to inject the Heparin into the patient's body. When the injection is finished the syringe 72 is removed and the door 40 is closed.

The infusion device 24 has a water resistant seal so the patient may shower without fear of wetting the assembly 20.

Also with the raised dome 34 the device 24 is protected while the patient sleeps and frequent replacements or reinsertions of the device by nurses are unnecessary. In this way the time of a nurse is conserved.

In FIG. 5 there is a slight modification of the infusion assembly 24 in that an intravenous or IV tube 74 projects rearwardly to receive the syringe 72 or IV solution. The inventor provides a clip 76 on the interior of door 40 to stabilize the tube 74. This is not essential but may assist in holding the infusion assembly 24. Also while not shown a U shaped clip or clips could depend downwardly from the crown of the done housing 34 to maintain the Heparin lock 60.

While a Heparin lock 60 is illustrated there may be other infusion device that are used where dislodgment and/or waterproofing is needed. The present invention will work for any such equipment requiring only dimensional charges to accomplish the intended results.

Turning now to FIGS. 7, 8 and 9 there is illustrated a modified infusion device 24 which is a subclavian catheter 78 occupying a relatively large horizontal area, compared to a Heparin lock 60. This is a device utilized with multiple categories of patients that is inserted in an incision 80 in the chest 82 of a person. In the incision there is inserted a tube 84 that usually is relatively long up to twelve inches and is bifurcated at 86 into two tubes 88 and 90. The ends 92 and 94 of tubes 88 and 90 may be fitted with any conventional caps or fittings 96 and 98 to receive a syringe for making an injection of drugs to the heart, or for withdrawing blood.

In the prior use of this subclavian catheter 78 a piece of tape 100 has used to hold the catheter 78 in place and thus in the incision 84. However the tape 100 cannot truly protect the subclavian catheter from dislodgment or from water and moisture. To that end the inventor has developed a modified protective cover 20' for an infusion device 24 that includes outwardly extending flanges 102, 104, 106 and 108 as in the previous device 20 that form a continuous annular flange (see FIG. 8). The flanges each include a waterproof adhesive to prevent moisture from entering the cover 20'. Extending upward from the flanges is a housing 34' of preferably clear plastic that has tapered opposed ends 110 and 112 and sides 114 and 116 that may be perpendicular or tapered from the plane of the flanges.

The top of the housing is hinged at 118 (see FIG. 9) as a living hinge so that it forms a door 110 that may be opened for access to the subclavian catheter 78.

The inventor also contemplates that on the underside of the door 120 a plurality of clips (not shown) may be installed to hold the tubes 84, 88 and 90 so that as the door is opened the tubes will be moved to a position for application of a syringe or syringes. With this structure the tape 100 is not absolutely essential.

Now with regard to the protective cover 20 there are various types of cross sectional shapes that may be utilized. In FIGS. 10a and 10b two such shapes as illustrated. In the case of FIG. 10a the sides and ends each taper upwardly and unwardly from the annular flanges. In FIG. 10b there are two sides that taper upwardly joining at approximately crown 122.

Finally, because rigidity is important to prevent damage or dislodgment of the catheter 78 the housing 34' could include a series of stiffening grooves 124.

The invention and its attendant advantages will be understood from the foregoing description and it will be apparent that various changes may be made in the form, construction and arrangements of the parts without departing from the spirit and scope thereof or sacrificing its material advantages, the arrangements herein before described being merely by way of example. I do not wish to be restricted to the specific forms shown or uses mentioned, except as defined in the accompanying claims, wherein various portions have been separated for clarity of reading and not for emphasis.

I claim:

1. A protective waterproof cover for use with an infusion device, said device generally permanently affixed to a person for a period of time wherein said device may receive drugs periodically, said cover to waterproof and protect said device from damage comprising:
   a transparent plastic housing surrounding and spaced from said infusion device including at least one flat surface and having a bottom edge and including strengthening means to restrict the collapsing of said housing to protect said infusion device from damage;
   an annular flange surrounding said housing at said bottom edge and extending radially outward from said housing, said flange having an underside;
   a waterproof releasable adhesive on said underside of said flange; and a waterproof door having an edge formed in said one flat surface to be opened for access to said infusion device and said door includes locking means to prevent entry of moisture when closed wherein said locking means includes a tongue projecting from said edge and a groove in said housing to receive said tongue therein by snapping action and lock the same.

2. A protective cover as defined in claim 1 wherein: said plastic housing is resilient and may be deformed to grip said infusion device for injection of drugs and upon release said housing will return to its original shape.

3. A protective cover as defined in claim 1 wherein: said housing is arcuate and at least one inflexible rib extends the length of said housing to stiffen said housing and restrict collapsing when force is applied to said housing.

4. A protective cover as defined in claim 1 wherein: said housing has a pair of opposed flat ends and said door is formed in one of said ends.

5. A protective cover as defined in claim 1 wherein: said at least one flat surface forms the top of said housing and said top is a hinged door for access to all of said device.

6. A protective cover as defined in claim 5 wherein: said door includes a living hinge in the form of a thinning of said plastic for a predetermined distance.

7. A protective cover as defined in claim 6 wherein: said housing includes a pair of opposed upwardly and inwardly tapered ends; and
said housing includes a pair of opposed upwardly and inwardly tapered sides between said end.

8. A protective cover as defined in claim 6 wherein said strengthening means are a plurality of stiffening parallel grooves formed in said housing to curtail collapsing of said housing when pressure is applied directly thereto.

9. A protective cover as defined in claim 1 wherein: said strengthening means are a plurality of stiffening parallel grooves formed in said housing to curtail collapsing of said housing when pressure is applied directly thereto.

* * * * *